(12) United States Patent
Otsubo et al.

(10) Patent No.: US 7,717,896 B2
(45) Date of Patent: May 18, 2010

(54) DISPOSABLE PULL-ON WEARING ARTICLE

(75) Inventors: Toshifumi Otsubo, Kagawa-ken (JP);
Naoto Ohashi, Kagawa-ken (JP);
Yusuke Kawakami, Kagawa-ken (JP);
Makoto Ichikawa, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 374 days.

(21) Appl. No.: 11/423,923

(22) Filed: Jun. 13, 2006

(65) Prior Publication Data
US 2006/0282057 A1 Dec. 14, 2006

(30) Foreign Application Priority Data
Jun. 14, 2005 (JP) .............................. 2005-173996

(51) Int. Cl.
*A61F 13/15* (2006.01)
*A61F 13/20* (2006.01)
(52) U.S. Cl. .............................. 604/385.27; 604/385.24
(58) Field of Classification Search ............ 604/385.11, 604/385.24–385.28
See application file for complete search history.

(56) References Cited
U.S. PATENT DOCUMENTS
6,352,528 B1 * 3/2002 Weber et al. ........... 604/385.03

FOREIGN PATENT DOCUMENTS

| JP | 4-371147 | | 12/1992 |
|---|---|---|---|
| JP | 4371147 | A | 12/1992 |
| JP | 8-507699 | | 8/1996 |
| JP | 8507699 | A | 8/1996 |
| JP | 3421030 | B2 | 4/2003 |
| JP | P3421030 | | 4/2003 |
| WO | 9203113 | A1 | 3/1992 |
| WO | WO 9203113 | A1 * | 3/1992 |
| WO | WO9203113 | A1 * | 3/1992 |

* cited by examiner

*Primary Examiner*—Melanie J Hand
(74) *Attorney, Agent, or Firm*—Lowe Hauptman Ham & Berner

(57) ABSTRACT

A disposable pull-on wearing article has its waist region divided into a front section and a rear section and connector sheet strips adapted to connect these two sections together. Each of the connector sheet strips has zones to be joined to the front sections and a non-joint zone interposed between the zones to be joined to the front and rear sections and adapted to be easily torn apart in the vertical direction of the article. The front and rear sections respectively have ears lying on the outer side. These ears have respective inner surface releasably joined to each other by a pressure-sensitive adhesive.

10 Claims, 7 Drawing Sheets test condition
size of test piece   width25mm×length100mm
inter-chuck distance   50mm
clamp margin   25mm
stress rate   200mm/min test condition
inter-chuck distance   100mm
clamp margin   25mm
stress rate   200mm/min

DISPOSABLE PULL-ON WEARING ARTICLE

BACKGROUND OF THE INVENTION

The present invention relates to a disposable pull-on wearing article such as a disposable pull-on diaper or training pants.

Conventionally, disposable pull-on diapers are well known in the form of a disposable pull-on wearing article. In one example of well known pull-on diapers, a front waist region and a rear waist region are joined together along transversely opposite side edges thereof and these side edges may be torn apart to take the diaper off from the wearer's body. For example, Japanese Unexamined Patent Application Publication No. 1992-371147 (hereinafter referred to "REFERENCE 1") discloses a disposable pant which can be used as the disposable pull-on diaper. In the case of the pant disclosed therein, a front waist region and a rear waist region are joined together along transversely opposite side edges thereof by use of a heat-sealing means. These side edges joined together in this manner have an appropriate strength such that the pant can be easily torn apart along these side edges to take the pant off from the wearer's body. In the pant, the front waist and rear waist regions are respectively provided with a plurality of thread-like elastic members extending in a transverse direction of these waist regions and attached in a stretched state thereto while the crotch region is provided with a plurality of thread-like elastic members attached in a stretched state thereto so as extend along the peripheral edges of the respective leg-holes.

There has already been proposed also a pull-on wearing article including panels which are elastically stretchable in the direction of the waist line and interposed between a front waist and rear waist regions. For example, National Publication of Translated Version No. 1996-507699 (referred to "REFERENCE 2") discloses a pull-on disposable diaper comprising an absorbent "chassis" and a pair of elastically stretchable "panels". This diaper further comprises a waist-hole and a pair of leg-holes. The "panels" which are elastically stretchable in the direction of the waist line are respectively provided in the vicinity of transversely opposite lateral regions of the wearer and attached to the "chassis" along predetermined joint lines. With this diaper put on the wearer's body, the "chassis" covers the front and rear waist regions as well as the crotch region of the wearer while the "panels" are elastically stretchable and contractible to make the diaper fit the lateral regions of the wearer's waist. When the diaper put on the wearer's body has been soiled with bodily discharges, the "panels" may be torn off from the "chassis" along the joint lines to take the diaper off from the wearer's body without the anxiety that the wearer's body might be soiled with bodily discharges. This diaper is further provided in the transversely middle zone on the rear waist region's outer surface with an adhesive tape tab used to secure the used diaper in a rolled up state for disposal.

Japanese Patent Publication No. 3421030 (hereinafter referred to "REFERENCE 3") discloses a pull-on undergarment. This undergarment comprises a front waist region, a rear waist region and a crotch region wherein the front and rear waist regions are connected together by nonwoven fabric strips adapted to be torn apart with the bare hands. Each of these nonwoven fabric strips extends in a longitudinal direction from one of leg-holes to a waist-hole and may be torn apart in the longitudinal direction to take the undergarment off from the wearer's body.

In the case of the pant disclosed in REFERENCE 1, each side edge of the front and rear waist regions comprises an inner sheet formed from a nonwoven fabric and an outer sheet formed from a lamination of a plastic film and a nonwoven fabric or the like. Assumed that the side edges of the front waist region each comprising a plurality of the sheet material layers are placed upon and joined to the side edges of the rear waist region by a heat-sealing means, each of the side edges of the pant would comprise four to six sheet material layers heat sealed together. An effort to tear these side edges joined together apart one from another to take the pant off from the wearer's body may sometimes peel the nonwoven fabric and the plastic film off from each other just along the joined zones and properly disconnect the front and rear waist regions from each other. However, this will be rarely achieved and, in many cases, the front and rear waist regions of the pant will be disconnected from each other with the nonwoven fabric and the plastic film torn not along the joined zones but around the joined zones. In other words, a caregiver for the wearer intending to take the pant off from the wearer's body must tear apart at least two or three layers of the sheet material at once with a considerable force. In addition to this inconvenience, it may be difficult for the caregiver to achieve this operation quickly since it will be rare that these layers of the sheet material are rectilinearly torn apart. Assumed that the waist surrounding elastic members and the leg-surrounding elastic members are attached in a stretched state to the pant, respectively, these elastic members may be peeled off from the nonwoven fabric and the plastic film and thereupon intensely contract just as the side edges of the pant are torn apart. These elastic members peeled off in this manner may painfully hit against the fingertips of the caregiver. Furthermore, the pant taken off from the wearer's body will be formed with a plurality of complicated gathers due to contraction of the waist-surrounding elastic members and the leg-surrounding elastic members and these complicated gathers will make it difficult to roll up or to fold the used pant for disposal in a manner such that the inner surface contaminated with bodily discharges might not be exposed.

The diaper disposed in REFERENCE 2 is said to ensure that the stretchable "panels" can be removed from the "chassis" along the joint lines of the "panels" and the "chassis". However, on the assumption that these joint lines are formed by a heat-sealing means the stretchable"panels" with the"chassis", operation of removing the "panels" from the "chassis" will really comprises, just like in the case of the pant disclosed in REFERENCE 1, operation of tearing the "panels" and/or the "chassis" along the joint lines. Such operation will require a considerable force and it may be difficult for the caregiver to achieve this operation quickly. Assumed that the stretchable "panels" include thread-like elastic members attached in a stretched state thereto, these elastic members intensely contract just as these "panels" are removed, and may painfully hit against the fingertips of the caregiver. Furthermore, upon removal of the "panels" from the "chassis", the transversely opposite lateral portions of the diaper are opened and, even after the diaper has been rolled up in the longitudinal direction and fixed in this rolled up state, the lateral portions remain opened. As a result, bodily discharges and odor may leak through these lateral portions remaining opened.

The diaper disclosed in REFERENCE 3 has no means for maintaining the used diaper in a rolled up state and it is likely that the soiled regions of the used diaper may be exposed and cause emission of odor.

SUMMARY OF THE INVENTION

In view of the problems as have been described above observed when the conventional wearing articles are taken off from the wearer's body, it is an object of the present invention to improve the known disposable pull-on wearing article.

According to the present invention, there is provided a disposable pull-on wearing article having a vertical direction, a back-and-forth direction and a transverse direction being orthogonal one to another, the article comprising: an annular waist region having a front section and a rear section; a crotch region extending between the front and rear sections of the annular waist region; a waist hole; a pair of leg-holes; a first elastic member extending along a peripheral edge of the waist holes; second elastic members extending along peripheral edges of the pair of leg-holes; and tear-apart lines being capable of separating the front and rear sections of the annular waist region and extending from the waist hole to each of the leg-holes in the vertical direction.

The article further comprises the following features:

A pair of connector sheets each has an outer surface, an inner surface opposite to the outer surface, joint zones extending on transversely opposite lateral zones of the outer surface in the vertical direction and a non-joint zone extending between the joint zones and being capable of tearing apart in the vertical direction for defining the tear-apart lines. The connector sheets each extends from the waist hole to each of the leg-holes in the vertical direction and the joint zones are permanently joined to inner surfaces of the transversely opposite lateral zones of the front and rear sections of the waist region which are separated from each other in the transverse direction. The front and rear sections of the waist region are provided contiguously to the lateral zones thereof with ears each lying outside the non-joint zone of each of the connector sheets and extending from the waist hole to each of the leg-holes, and each pair of the ears facing each other have respective inner surfaces releasably joined to each other with an adhesive. At least the non-joint zone of each of the connector sheets including none of the first and second elastic members.

According to a preferred embodiment of the invention, at least one of the front and rear sections is provided with an elastic member extending along a waist line and a segment of the elastic member extending between the joint zones is attached in a stretched state thereto but remaining segments extending toward the ears beyond the joint zones are attached thereto not in a stretched state.

According to the embodiment of the invention, the waist region is provided in a vicinity of the transversely opposite lateral portions with a pair of sheet strips adapted to connect the transversely opposite lateral portions of the front section to the transversely opposite lateral portions of the rear section and to facilitate the formation of the tear-apart lines. This unique arrangement facilitates the used diaper soiled with bodily discharges to be quickly taken off from the wearer's body merely by tearing apart these sheet strips. For disposal of the diaper taken off in this manner may be rolled up form the front section toward the rear section or vice versa and a pressure-sensitive adhesive coated on the ears of the front or rear section may be utilized to fasten the diaper rolled up in this manner to prevent bodily discharges and odor thereof from leaking beyond the lateral portions of this rolled up diaper. In addition, the sheet strips include none of elastic members extending in the direction of the waist line and therefore operation of tearing these sheet strips in the vertical direction is not affected by the presence of these elastic members.

According to another embodiment of the invention, while the article includes the elastic member extending in the direction of the waist line and attached in a stretched state thereto, this elastic member is not in stretched state in each pair of the ears releasably joined to each other. Therefore, it is unlikely that these ears might be easily peeled off from each other due to stretching and contraction of the elastic member.

DETAILED DESCRIPTION OF THE PREFERRED EMBODIMENTS

Details of a disposable pull-on wearing article will be more fully understood from the description of a disposable pull-on diaper as an embodiment of the invention given hereunder with reference to the accompanying drawings.

Figure 1:
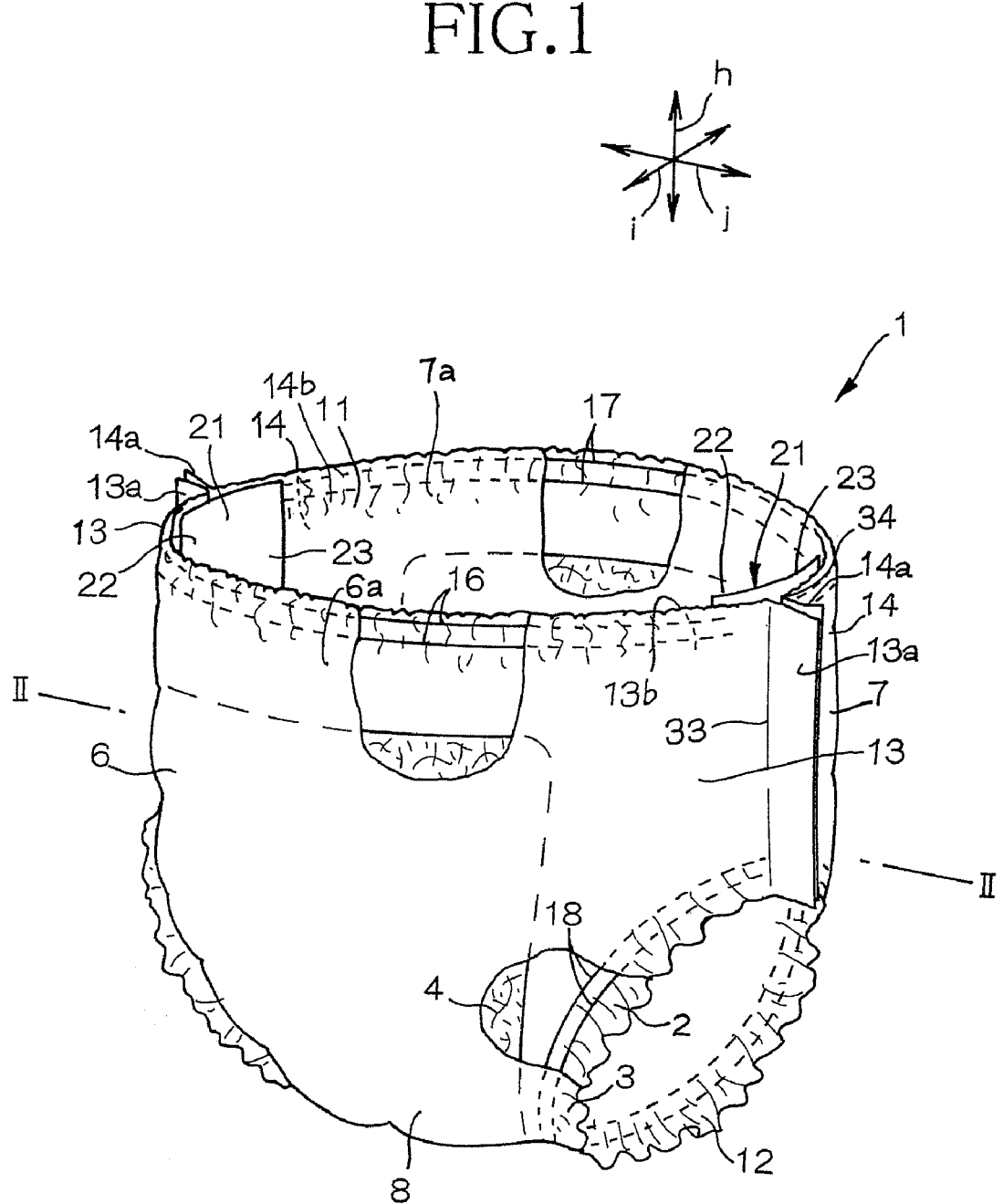
FIG. 1 is a partially cutaway perspective view showing a pull-on diaper.
Figure 2:
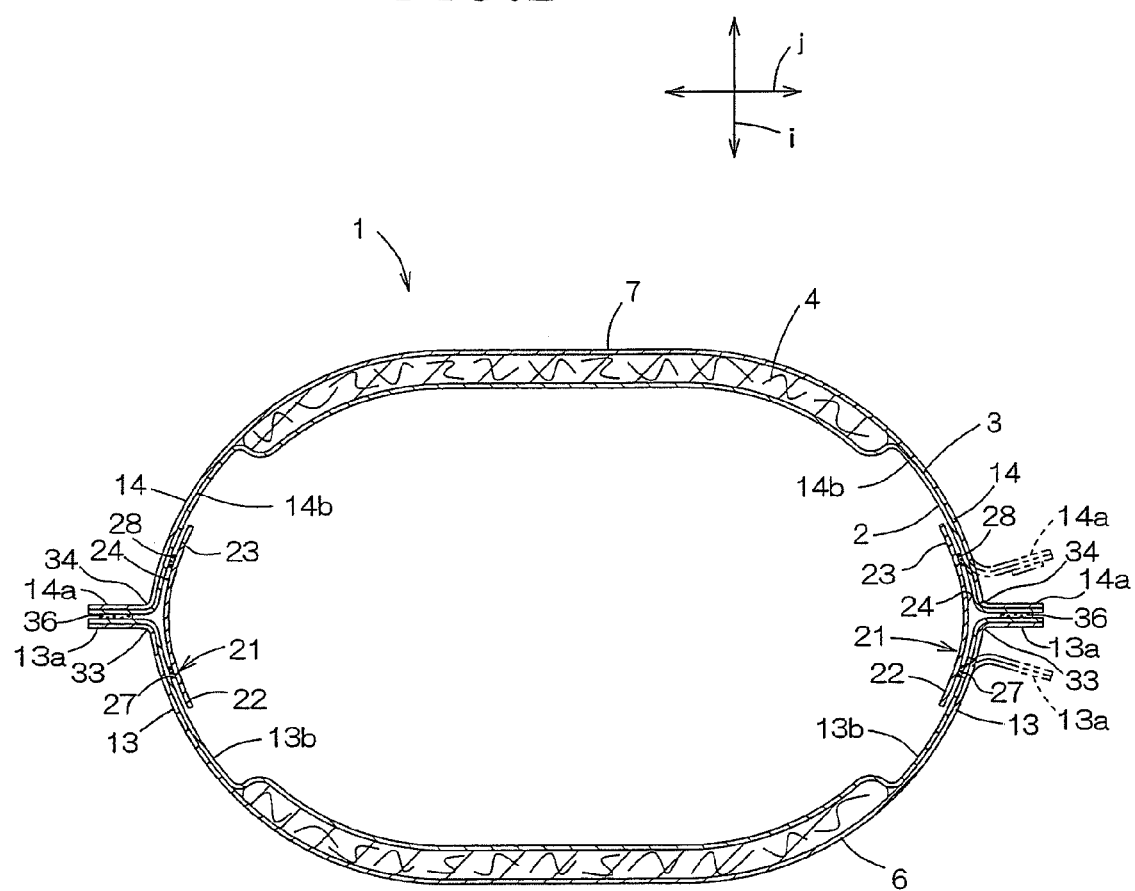
FIG. 2 is a sectional view taken along the line II-II in FIG. 1.
Figure 3:
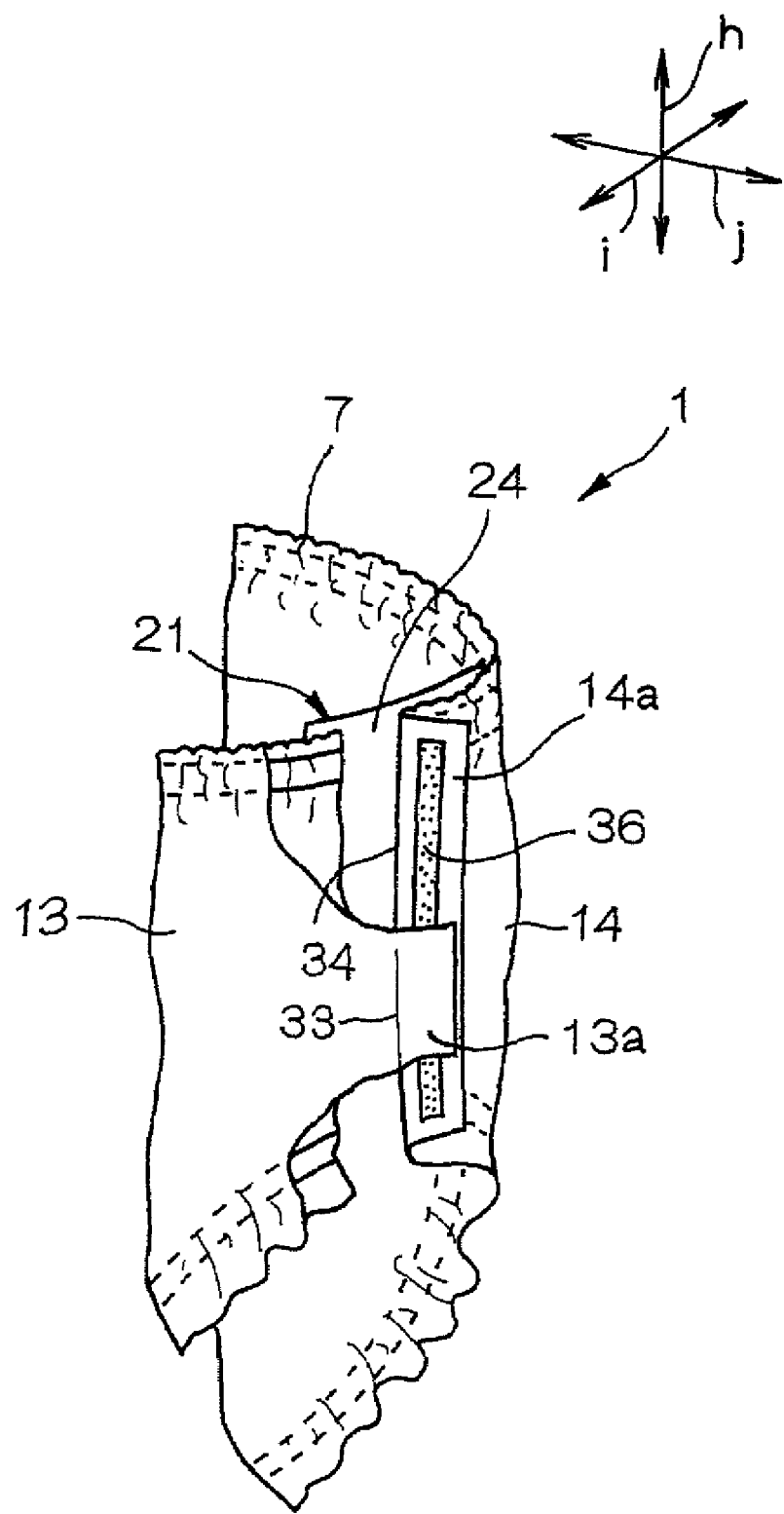
FIG. 3 is a partially enlarged perspective view partially showing the pull-on diaper.

FIG. 1 is a perspective view showing a pull-on diaper 1, FIG. 2 is a sectional view taken along the line II-II in FIG. 1, and FIG. 3 is a partial view showing the pull-on diaper 1. In FIGS. 1 and 3, the diaper 1 is shown as partially cutaway. The diaper 1 is composed of a liquid-pervious topsheet 2, a liquid-impervious backsheet 3 and a body fluid absorbent core 4 sandwiched between these two sheets 2, 3. The diaper 1 further is configured to define a front waist region 6, a rear waist region 7 and a crotch region 8 destined to cover a front waist region, a rear waist region and a crotch region of the wearer. In the respective regions 6, 7, 8, both the topsheet 2 and the backsheet 3 extend outward beyond a peripheral edge of the core 4 and are joined to each other by hot melt adhesives (not shown) in the respective regions thereof extending outward beyond the peripheral edge of the core 4. The front waist region 6 defines an upper end 6a and a pair of transversely opposite lateral portions 13 and the rear waist region 7 also defines an upper end 7a and a pair of transversely opposite lateral portions 14. Along both lateral portions of the diaper 1, each pair of the lateral portions 13, 14 being circumferentially adjacent to each other in a direction of the waist line are connected to each other with interposition of a connector sheet strip 21. Consequentially, the front and rear waist regions 6, 7 are annularly connected to each other whereupon the front and rear waist regions 6, 7 form a waist-hole 11 and, at the same time, cooperate with the crotch region 8 to form a pair of leg-holes 12. The respective lateral portions 13, 14 outwardly terminating in vertically extending ears 13a, 14a, respectively, which are put flat and releasably joined together. The front and rear waist regions 6, 7 are provided with elastic members 16, 17 extending along front and rear waist lines, respectively, so as to extend along a peripheral edge of the waist-hole 11. In the crotch region 8, leg surrounding elastic members 18 extend in a stretched state along a peripheral edge of this leg-hole 12. These elastic members 16, 17, 18 are sandwiched between the topsheet 2 and the backsheet 3 and joined in a stretched state to at least one of these sheets 2, 3 by hot melt adhesives (not shown). The diaper 1 has a vertical direction, a back-and-forth direction and a transverse direction designated by h, i and j, respectively, and a waist surrounding direction along which the peripheral edge of the waist-hole 11 extends.

Figure 5:
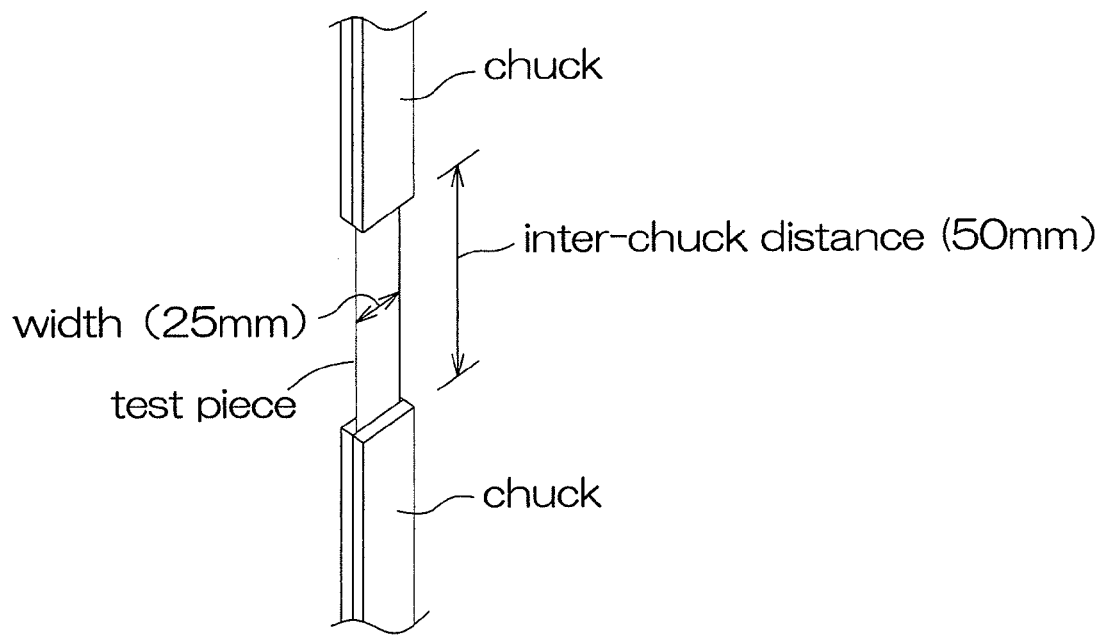
FIG. 5 is a diagram schematically illustrating a method for measurement of tensile strength.
Figure 6:
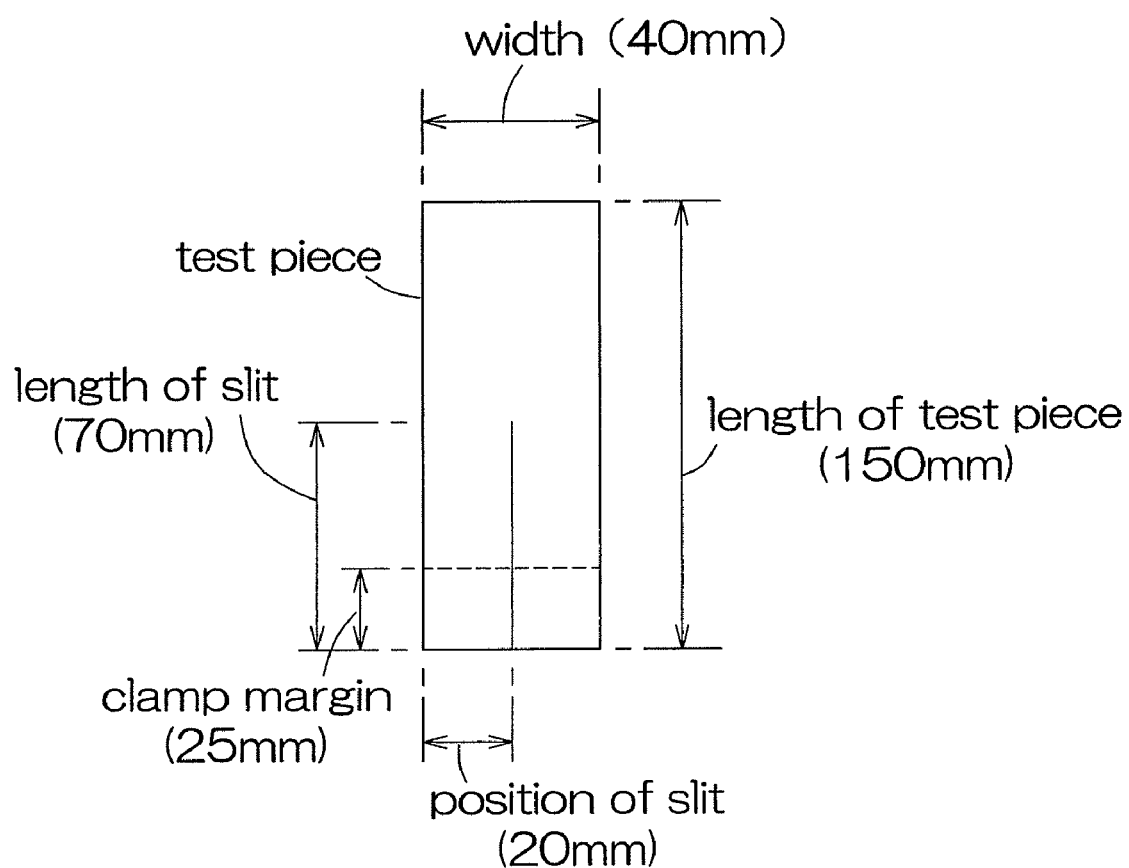
FIG. 6 is a diagram schematically illustrating a test piece used for measurement of tear strength.
Figure 7:
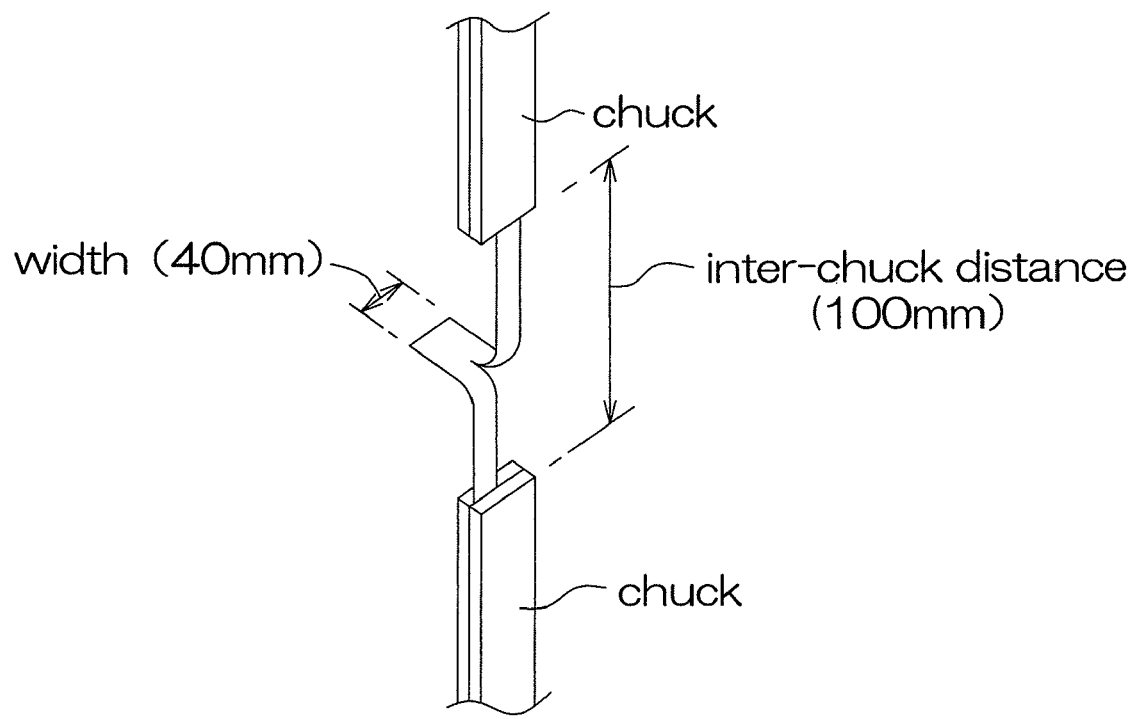
FIG. 7 is a diagram schematically illustrating a method for measurement of tear strength.

Each of connector sheets 21 adapted to connect the front waist region 6 and the rear waist region 7 cooperating with each other to form the annular waist region is provided along the vicinity of its front side edge 22 and rear side edge 23 as viewed in the waist surrounding direction with joint zones 27, 28 extending in the vertical direction h (See FIG. 2) to be permanently joined to respective inner surfaces 13b, 14b of the lateral portions 13, 14 and further provided between these joint zones 27, 28 with an non-joint zone 24 to be left free from both the front region 6 and the rear regions 7. The non-joint zone 24 extends between the waist-hole 11 and the leg-hole 12 in the vertical direction h. The connector sheet strip 21 has in the non-joint zone 24 a tensile strength and a tear strength which are measured in manners as illustrated in FIGS. 5 through 7. Specifically, in order to prevent the non-joint zone 24 from being easily broken even if the non-joint zone 24 is strained in the waist surrounding direction as the diaper is put on the wearer's body, the non-joint zone 24 preferably has the tensile strength of at least 8N/width of 25 mm in the waist surrounding direction. The non-joint zone 24 is adapted to be linearly torn in the vertical direction h from the waist-hole 11 to the leg-hole 12 when the diaper 1 is taken off from the wearer's body. To make this possible, the non-joint zone 24 preferably has the tear strength of 0.1 to 12N in the vertical direction h. The transversely opposite lateral portions 13 of the front waist region 6 have the ears 13a which extend from the respective joined zones 27 toward the rear waist region 7 as viewed in the waist surrounding direction while the transversely opposite lateral portions 14 of the rear waist region 7 have the ears 14a which extend from the respective joined zones 28 toward the front waist region 6 as viewed in the waist surrounding direction. These ears 13a, 14a are laid outside the non-joint zones 24 and folded outwardly of the diaper 1 along respective folds 33, 34 so that each pair of the ears 13a, 14a may be opposed to each other. One of these ears 13a, 14a opposed to each other may be coated on the inner surface thereof with a pressure-sensitive adhesive 36 to bond these ears 13a, 14a together in a releasable manner. To take the diaper 1 off from the wearer's body, the ears 13a are peeled off from the ears 14a as indicated by imaginary lines in FIG. 2 and thereby the connector sheets 21 are exposed outwardly of the diaper 1. Then, the connector sheets 21 are torn apart along the respective non-joint zones 24 in the vertical direction h. Assumed that the elastic members 16, 17 extending along the front and rear waist lines as well as the leg-surrounding elastic members 18 do not extend to the ears 13a, 14a beyond the joint zones 27, 28, it is not apprehended that contraction of these elastic members 16, 17, 18 might form gathers. Consequentially, the ears 13a, 14a will be sufficiently flat to facilitate these ears 13a, 14a to be joined together by the adhesive 36 and to eliminate an anxiety that these ears 13a, 14a might be unintentionally peeled off from each other. While an alternative embodiment of the invention may be contemplated, in which the elastic members 16, 17 extending along the front and rear waist lines as well as the leg-surrounding elastic members 18 extend to the ears 13a, 14a beyond the joint zones 27, 28, it should be noted that, in this case, the segments of these elastic members 16, 17, 18 are preferably in a non-stretched state. The intended purpose of the adhesive 36 is not to maintain the front and rear waist regions 6, 7 of the diaper 1 joined in the annular state but to bond the opposed ears 13a, 14a temporarily, i.e., in a releasable manner so that the surface of the adhesive 36 may be stained even during actual use of the diaper 1 and the diaper 1 soiled with bodily discharges may be rolled up for disposal thereof in a manner as will be described.

In the diaper 1, the non-joint zones 24 of the respective connector sheet strips 21 include none of the elastic members 16, 17 extending along the front and rear waist lines and the leg-surrounding elastic members 18 and therefore there is no anxiety that the presence of these elastic members 16, 17, 18 might make it difficult to tear apart the respective non-joint zones 24 in the vertical direction h. In addition, there is no anxiety that the elastic members might acutely hit against the fingertips of a caregiver for the wearer tearing apart the diaper 1 upon intense contraction of the elastic members having been in a stretched state contract as the conventional pull-on diaper has been the case. The diaper 1 may be alternatively exploited, wherein the connector sheet strips 21 has a color distinguished from that of the ears 13a, 14a so that the non-joint zones 24 of the respective connector sheet strips 21 can be easily identified.

Figure 4:
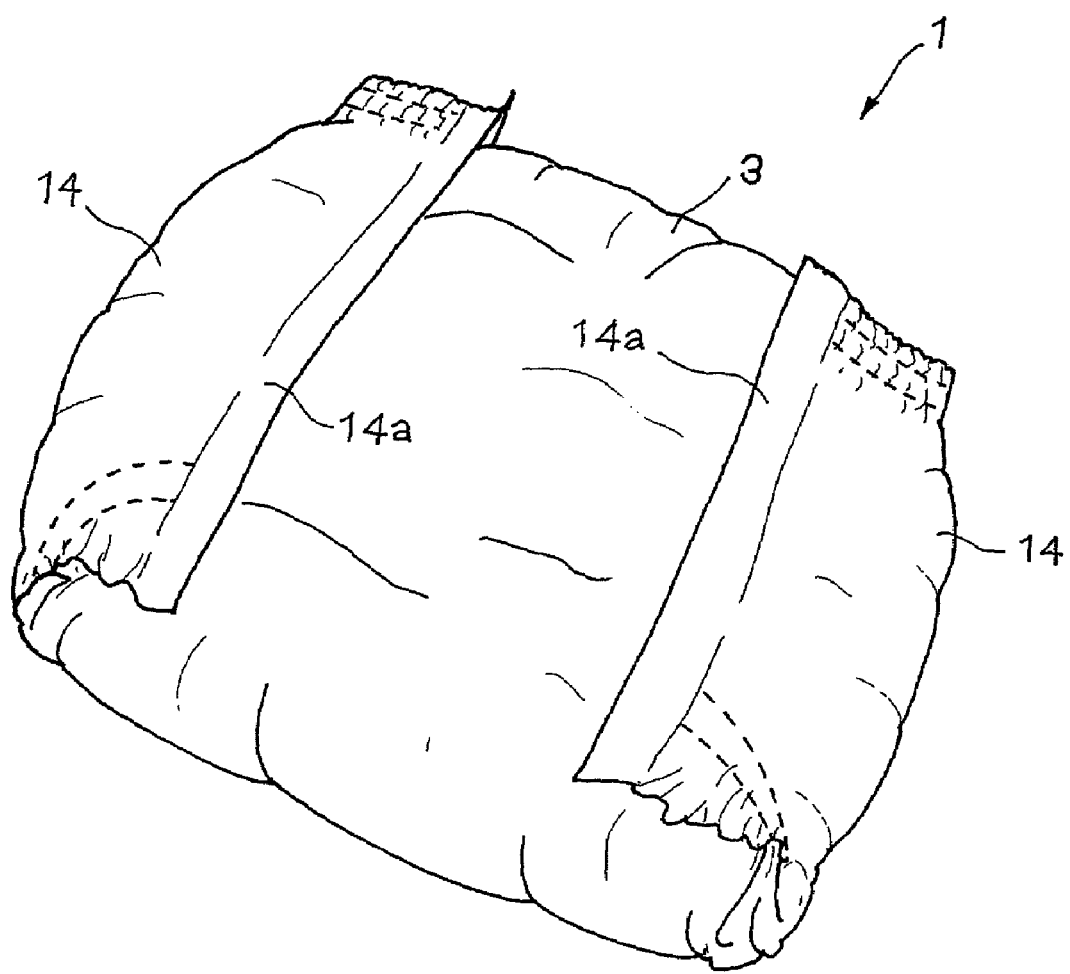
FIG. 4 is a perspective view showing the diaper as rolled up.

FIG. 4 is a perspective view showing the diaper 1 which has been taken off from the wearer's body by tearing apart the connector sheet strips 21 and then rolled up from the front waist region 6 toward the rear waist region 7 with the topsheet 2 contaminated with bodily discharges lying on the inside. After has been rolled up in this manner, the ears 14a of the rear waist region 7 may be folded back and fixed to the backsheet 3 by the adhesive 36 to keep this rolled up diaper 1 effectively closed along the lateral portions thereof and thereby to prevent bodily discharges as well as odor from leaking beyond these lateral portions. Assumed that the diaper 1 soiled in the crotch region 8 with bodily discharges is rolled up from the front waist region 6 toward the rear waist region 7 or vice versa so as to wrap around the soiled crotch region 8 with the unsoiled front and rear waist regions 6, 7, there is no anxiety that bodily discharges and odor might leak beyond the respective upper ends 6a, 7a of the diaper 1 (See FIG. 1) but it is likely that bodily discharges and odor might leak beyond the transversely opposite lateral portions of the diaper 1. Such likelihood can be effectively prevented by closing the lateral portions by using the ears 14a, 14a and the adhesive 36 as illustrated by FIG. 4.

To exploit the present invention, a stock material for the connector sheet strip 21 may be selected from the group, for example, consisting of a nonwoven fabric comprising component fibers made of thermoplastic synthetic resin such as polyethylene, polypropylene or polyester, a film made of such synthetic resin, a lamination sheet comprising the nonwoven fabric and the film as described just above. Such nonwoven fabric or film may be provided with one or more perforated lines extending in the vertical direction h so as to be easily torn apart. As far as the nonwoven fabric composed of fibers prominently oriented in a specific direction or the film in which the macromolecular strands prominently oriented in a specific direction, the nonwoven fabric or the film may be used so that the specific direction may be conformity with the vertical direction h of the diaper 1 to ensure that the connector sheet strip 21 can be easily torn apart rectilinearly in the vertical direction h.

A stock material for the topsheet 2 may be selected from the group consisting of a nonwoven fabric made of thermoplastic synthetic resin fibers with a basis weight of 10 to 30 g/m² and a porous film made of thermoplastic synthetic resin with a thickness of 10 to 30 μm.

A stock material for the backsheet 3 may be selected from the group, for example, consisting of a film made of thermoplastic synthetic resin with a thickness of 20 to 50 μm and a composite sheet comprising such film and nonwoven fabric made of thermoplastic synthetic resin fibers with a basis weight of 20 to 50 g/m² which are intermittently joined to each other.

The body fluid absorbent core 4 may be formed from a mixture of fluff pulp and super-absorbent polymer particles wrapped with a sheet material such as a tissue paper or nonwoven fabric having high liquid-permeability and high liquid-diffusivity or fluff pulp wrapped with such sheet material.

Along the transversely opposite lateral portions 13, 14 of the front and rear waist regions 6, 7, respectively, the topsheet 2 and the backsheet 3 are joined together by the known adhesion or heat-sealing technique to form the composite sheet and/or this composite sheet includes the elastic members 16, 17 extending along the front and rear waist lines as well as the leg-surrounding elastic members 18. Therefore, the transversely opposite lateral portions 13, 14 have the tensile strength and the tear strength both higher than those of the connector sheet strips 21 and it is unlikely that these lateral portions 13, 14 might be torn easier than the connector sheet strips 21 when the diaper 1 is taken off from the wearer's body. In the case of the diaper 1 according to the invention, the lateral portions 13 and/or the lateral portions 14 may be formed from one of the topsheet 2 and the backsheet 3 so far as one of these topsheet and backsheet 3 has the tensile strength as well as the tear strength higher than those of the connector sheet strip 21. Furthermore, the lateral portions 13 and/or the lateral portions 14 may be formed from a third sheet provided separately of both the topsheet 2 and the backsheet 3 and having the tensile strength as well as the tear strength higher than the connector sheet strip 21. The lateral portions 13, 14 are joined together by the known heat-sealing technique or adhesion along the respective joint zones 27, 28 with a sufficiently high peel strength to eliminate the possibility that the lateral portions 13, 14 might be peeled off from each other as the diaper 1 is put on or taken off from the wearer's body.

FIG. 5 is a diagram illustrating a method for measurement of tensile strength presented by the sheet material used as the connector sheet strip 21 together with a test piece used for this measurement. The test piece is made so as to have a longitudinal direction in conformity with the direction of the diaper's waist line and attached to the tensile tester with an inter-chuck distance of 50 mm. This test piece is stretched at a stress rate of 200 mm/min to determine a value of the ultimate load until a moment of breakage as the tensile strength.

FIGS. 6 and 7 are diagrams respectively illustrating a test piece used for measurement of tear strength of the sheet material used as the connector sheet strip 21 and a method for this measurement. The test piece is made so that a longitudinal direction of the test piece itself as well as a slit thereof may be in conformity with the vertical direction h of the diaper 1. The test piece is attached to the tensile tester with clamp margins of approximately 25 mm, respectively, so that an inter-chuck distance of 100 mm may be left free. The test piece is stretched at a stress rate of 200 mm/min and a value of the maximum load resulting in breakage is determined as the tear strength.

While the present invention has been described hereinabove with respect to the disposable pull-on diaper, this invention may be applicable to the other disposable wearing article such as training pants, pants for incontinent patient or sanitary shorts. In the illustrated embodiment, the connector sheet strips 21 are provided in the vicinity of the transversely opposite lateral portions such that each of the connector sheet strips 21 is substantially bisected and the front half is provided on the front waist region 6 and the rear half is provided on the rear waist region 7. However, positions at which the connector sheet strips 21 are provided are not specified. Specifically, it is also possible without departing from the spirit and the scope of the invention to provide the connector sheet strips 21 optionally at the positions put aside from the lateral portions of the waist region toward the wearer' abdomen or back.

The present invention makes it possible to produce the pull-on disposable wearing article adapted to be taken off from the wearer's body as the transversely opposite lateral portions of the waist region are easily torn apart and, after taken off, to be rolled up for disposal so as to prevent leak of bodily discharge and odor.

The entire discloses of Japanese Patent Application No. 2005-173996 filed on Jun. 14, 2005 including specification, drawings and abstract are herein incorporated by reference in its entirety.

What is claimed is:

1. A disposable pull-on wearing article having a vertical direction, a back-and-forth direction and a transverse direction being orthogonal one to another, said article comprising:
   an annular waist region having a front section and a rear section;
   a crotch region extending between said front and rear sections of said annular waist region;
   a waist hole;
   a pair of leg-holes;
   a first elastic member extending along a peripheral edge of said waist hole;
   second elastic members extending along peripheral edges of said leg holes; and
   a pair of connector sheets connecting transversely opposite lateral zones of said front and rear sections, each of said connector sheets extending in said vertical direction from said waist hole to one of said leg holes and having an outer surface,
      an inner surface opposite to said outer surface,
      two joint zones on said outer surface, extending in said vertical direction and being permanently directly joined to inner surfaces of the respective lateral zones of said front and rear sections, and
      a non-joint zone extending in said transverse direction between said joint zones and defining a tearable line which, when torn in said vertical direction, disconnects the respective lateral zones of said front and rear sections from each other;
   each of said front and rear sections of said waist region further comprising ear portions which are contiguous to the lateral zones of said section and extend in the transverse direction away from the waist hole;
   each of said ear portions being located outside said non-joint zone of the respective one of said
   each pair of said ear portions facing each other having respective inner surfaces releasably, directly and adhesively joined to each other; and
   said non-joint zone of each of said connector sheets being free of said first and second elastic members.

2. The wearing article as defined by claim 1, wherein the connector sheets are tearable along the non-joint zones in the vertical direction.

3. The wearing article as defined by claim 1, wherein each of the connector sheets has a color distinguished from that of the ear portions to visually identify the non-joint zones.

4. The wearing article as defined by claim 1, wherein said lateral zones of said front and rear sections of said waist region are configured integrally from at least one sheet of said front and rear sections.

5. The wearing article as defined by claim 1, wherein said lateral zones of said front and rear sections are configured integrally from two sheets of said front and rear sections.

6. The wearing article as defined by claim 1, wherein said ear portions are free of elastic members.

7. The wearing article as defined by claim 1, wherein each of said ear portions comprises a segment of at least one of said first and second elastic members, said segment being attached to the ear portion in a non-stretched state.

8. The wearing article as defined by claim 1, wherein the inner surfaces of the connector sheets and the inner surfaces of the transversely opposite lateral zones of said front and rear sections are adapted to face a wearer in use.

9. The wearing article as defined by claim 8, wherein the non-joint zones of the connector sheets are free of direct attachment to the front and rear sections.

10. The wearing article as defined by claim 9, wherein the entire inner surfaces of the connector sheets are adapted to directly contact the wearer in use.

\* \* \* \* \*